(12) United States Patent
Munos (10) Patent No.: US 11,139,050 B2
(45) Date of Patent: Oct. 5, 2021

(54) SYSTEMS AND METHODS FOR PRE-QUALIFYING CLINICAL TRIAL POPULATIONS

(71) Applicant: Transparency Life Sciences, Inc., New York, NY (US)

(72) Inventor: Bernard Munos, New York, NY (US)

(73) Assignee: Transparency Life Sciences, Inc., New York, NY (US)

(*) Notice: Subject to any disclaimer, the term of this patent is extended or adjusted under 35 U.S.C. 154(b) by 1193 days.

(21) Appl. No.: 14/466,257

(22) Filed: Aug. 22, 2014

(65) Prior Publication Data
US 2015/0058033 A1 Feb. 26, 2015

Related U.S. Application Data

(60) Provisional application No. 61/869,090, filed on Aug. 23, 2013.

(51) Int. Cl.
*G16H 10/20* (2018.01)
*G16H 10/40* (2018.01)
*G16H 50/70* (2018.01)

(52) U.S. Cl.
CPC .................. *G16H 10/20* (2018.01)

(58) Field of Classification Search
CPC .... G06F 19/363; G06F 19/3418; G06F 1/163; G16H 10/20; G16H 50/30; G16H 50/70;
(Continued)

(56) References Cited

U.S. PATENT DOCUMENTS 5,941,820 A * 8/1999 Zimmerman .......... G16H 40/63
600/300
7,415,447 B2 8/2008 Shiffman et al.
(Continued)

FOREIGN PATENT DOCUMENTS

WO 0154650 A2 8/2001

OTHER PUBLICATIONS

Holly K. Tabor, Neil J. Risch & Richard M. Myers, Candidate-gene approaches for studying complex genetic traits: practical considerations, Nature Reviews Genetics, May 2002, All pages (Year: 2002).*

(Continued)

*Primary Examiner* — Elaine Gort
*Assistant Examiner* — Teresa S Williams
(74) *Attorney, Agent, or Firm* — Wolf, Greenfield & Sacks, P.C.

(57) ABSTRACT

Provided are systems and methods for pre-qualification of candidate patient populations. The systems and methods can be are configured for inexpensive, selective, and lightweight procedures that identify patients against desired criteria. In some implementations, willing participants are enrolled in pre-treatment execution of a clinical trial. The participants are issued telemedicine monitoring devices for capturing and reporting health information. For example, non-invasive monitoring devices can be issued to track mobility, exertion, blood pressure, heart rate, brain activity, among other options. The participants can be monitored for time periods similar to actual trial execution phases (e.g., monitoring periods of years can be used) or monitored for any length of time to develop comparable clinical histories for the participants.

11 Claims, 3 Drawing Sheets

(58) Field of Classification Search
CPC .. G16H 10/60; G01N 2800/52; A61B 5/7275; A61B 5/0022; A61B 5/4088; A61B 5/05; A61B 5/163
USPC ......................................... 705/2, 3
See application file for complete search history.

(56) References Cited

U.S. PATENT DOCUMENTS

| | | | |
|---|---|---|---|
| 8,566,121 B2 * | 10/2013 | Ramasubramanian | G06F 19/3456 705/3 |
| 2003/0225856 A1 * | 12/2003 | Pietrowski | G06F 19/3418 709/217 |
| 2004/0006553 A1 * | 1/2004 | de Vries | G06F 19/363 |
| 2004/0078220 A1 | 4/2004 | Jackson | |
| 2006/0031101 A1 * | 2/2006 | Ross | G06F 19/3418 705/3 |
| 2010/0088245 A1 * | 4/2010 | Harrison | G06Q 10/10 705/317 |
| 2012/0203078 A1 | 8/2012 | Sze et al. | |
| 2013/0144644 A1 | 6/2013 | Simpson | |
| 2013/0197894 A1 * | 8/2013 | Sablinski | G16H 10/20 703/11 |
| 2020/0381087 A1 * | 12/2020 | Ozeran | G16H 10/20 |

OTHER PUBLICATIONS

Notification of the International Search Report and the Written Opinion of the International Searching Authority from corresponding PCT/US2014/052265 dated Dec. 2, 2014.

* cited by examiner

SYSTEMS AND METHODS FOR PRE-QUALIFYING CLINICAL TRIAL POPULATIONS

RELATED APPLICATIONS

This application claims priority under 35 U.S.C. § 119(e) to U.S. Provisional Application No. 61/869,090, entitled "SYSTEMS AND METHODS FOR PRE-QUALIFYING CLINICAL TRIAL POPULATIONS," filed on Aug. 23, 2013, which application is incorporated herein by reference in its entirety.

BACKGROUND

Conventional approaches for clinical trial execution invoke slow and time consuming patient enrollment processes. Typically, patient enrollment requires significant support and infrastructure, as enrollment is done at hospitals and/or through doctors. In some examples, the hospitals and/or doctors do not even focus on clinical trial development. Rather, they are engaging in trial definition and/or execution as a sideline activity, while continuing the normal practice of seeing and treating patients.

Trial administration is further complicated by appropriate selection of trial participants. Some conventional methodologies attempt to screen out members of candidate patient pools by having the hospital and/or doctors administer "run-in" periods where placebo effect parameters can be monitored and statistical anomalies can be excluded from participation. However, these conventional run-in periods are as difficult to administer as the trial, and can increase drop-out rates. Other problems can be generated by conventional run-in periods, including skewing results and jeopardizing validity of a trial through unintended mechanisms.

SUMMARY

Conventional approaches to patient enrollment for clinical trials leaves much to be desired. For example, there is a need for streamlined patient enrollment processes. Such streamlined enrollment processes can provide for fast, efficient, and selective enrollment. Further, there is a need for enrollment processing that can accurately identify patient populations having desired characteristics and further that is capable of weeding out patients within that population having undesirable characteristics prior to starting a clinical trial. There is also a need for a patient enrollment process that does not overburden the candidate patients. It is realized that conventional enrollment results in significant drop-out and may reduce the likelihood of patients completing a trial protocol due to frustration, fatigue, repetitiveness, burden, among other reasons.

In broad overview, various aspects relate to systems and methods for pre-qualification of candidate patient populations. According to various embodiments, the systems and methods are configured for inexpensive, selective, and lightweight procedures that identify patients against desired criteria. In some implementations, willing participants are enrolled in pre-treatment execution of a clinical trial. The willing participants are issued telemedicine monitoring devices for capturing and reporting detailed health information. For example, non-invasive monitoring devices can be issued to track mobility, exertion, blood pressure, heart rate, brain activity, among other options. The willing participants can be monitored for time periods similar to actual trial execution phases (e.g., monitoring periods of years can be used) or monitored for any length of time to develop comparable clinical histories for the participants. It is realized that it is not feasible to implement conventional approaches (e.g., convention run-in periods) to obtain such data. Administrative and systematic issues make such conventional approaches entirely unsuited to developing a comprehensive pre-qualification system.

In some embodiments, the pre-treatment execution includes collection of clinical history data without administration of clinical trial treatments. For example, the candidates continue whatever treatment regimen (including no treatment) they are currently taking, and monitoring devices record data on respective medical characteristics (e.g., biological, physiological, verbal, motion, sight, blood pressure, respirations, brain activity, tactile response/sensation, etc.). In some embodiments, the participants can be taking prescribed medications during pre-treatment execution under the direction of their physician. In further examples, selection criteria may require that candidates are undergoing treatment with a specific medication.

By capturing detailed patient information over time, the system is configured to identify uniquely suited patients for a variety of clinical trial and trial characteristics. In some examples, even within patient populations meeting threshold criteria the system can further filter out candidates. For example, detailed monitoring of target medical characteristics can be analyzed by the system to identify candidates having high variability in their readings. Highly variable readings (e.g., widely varying blood pressure) may skew clinical trial results on a blood pressure reducing drug. An improved test population can be identified for executing the clinical trial by eliminating highly variable candidates. In other examples, the system can also detect candidate patients who respond under a placebo effect and filter out the same as potential candidates. According to some embodiments, the system enables filtering of candidate populations with precision and accuracy based on detailed tracking of trial measurement characteristics. Further, the system enables filtering of candidate populations within any targeted criteria to improve consistency and limit variables that may skew results.

According to one aspect, the system enables highly specified candidate patient pools. These highly specified patient pool improve over known systems, in which failed enrollment targets can jeopardize a clinical trial execution. In some conventional approaches, clinical trial sites enroll single patients or even no patients during trial execution. The non-participating sites waste valuable time. Various embodiments, of the system and method address these issues.

According to another aspect, a system for prequalifying patient populations is provided. The system comprises at least one processor operatively connected to a memory; a registration component, executed by the at least one processor, configured to register candidate patients and associate remote monitoring devices to registered patients; a collection component, executed by the at least one processor, configured to receive health information from the remote monitoring devices over a period of time; and an analysis component, executed by the at least one processor, configured to qualify candidate patients according to a patient model, wherein the patient model defines a first characteristic for a disease or ailment, and further defines at least a second characteristic associated with disease progression or response to current treatment.

In one embodiment, the system further comprises a consent component configured to manage patient consent to participate in a clinical trial. In one embodiment, the system is further configured to communicate to a qualified candidate patient pool to start the clinical trial. In one embodiment, the system is configured to accept definition of a patient model based on medical characteristics to evaluate during execution of the clinical trial. In one embodiment, the analysis component is configured to identify improper candidates responsive to variations in the received health information. In one embodiment, the analysis component is further configured to generate a threshold variation in measurements of the health information responsive to analyzing the stored health information.

In one embodiment, the analysis component is further configured to generate the threshold variation to exclude any candidate patient having one or more measurements exceeding two standard deviations from historical patient data. In one embodiment, the analysis component is further configured to analyze historical patient data having common characteristics defined by a patient model; and test the historical patient data against all historical patient data. In one embodiment, the analysis component is further configured to generate the patient model responsive to analyzing stored health information and any associated condition.

According to one aspect, a computer implemented method for pre-qualifying patient populations is provided. The method comprises registering, by a computer system, candidate patients for pre-treatment trial monitoring; associating, by the computer system, remote monitoring devices to registered patients; executing, by the computer system, a pre-treatment monitoring phase, wherein the act of executing includes receiving health information from the remote monitoring devices over a period of time; and qualifying, by the computer system, candidate patients according to a patient model, wherein the act of qualifying includes comparing the health information against the patient model including a first characteristic for a disease or ailment, and at least a second characteristic associated with disease progression or response to current treatment.

In one embodiment, the method further comprises generating, by the computer system, a qualified pool of candidate patients for a respective clinical trial responsive to the act of qualifying. In one embodiment, the method further comprises managing, by the computer system, patient consent to participate in a clinical trial. In one embodiment, the method further comprises qualifying, by the computer system, the candidate patient pool to start the clinical trial. In one embodiment, the method further comprises accepting, by the computer system, definition of a patient model based on medical characteristics to evaluate during execution of the clinical trial. In one embodiment, the method further comprises identifying, by the computer system, improper candidates responsive to variations in the received health information. In one embodiment, the method further comprises automatically generating, by the computer system, a threshold variation in measurements of the health information responsive to analyzing stored health information.

In one embodiment, the method further comprises automatically generating, by the computer system, the threshold variation to exclude any candidate patient having one or more measurements exceeding two standard deviations from historical patient data. In one embodiment, the method further comprises analyzing, by the computer system, historical patient data having common characteristics defined by a patient model; and testing, by the computer system, the historical patient data against all historical patient data. In one embodiment, the method further comprises automatically generating, by the computer system, the patient model responsive to analyzing stored health information and any associated condition.

According to one aspect, a patient selection system is provided. The system comprises at least one processor operatively connected to a memory; a communication component, executed by the at least one processor, configured to register patient monitoring devices; receive physiologic or biometric data on candidate patients from the patient monitoring devices; an analysis component, executed by the at least one processor, configured to identify statistical variation in a respective candidate patient's symptoms or physiologic condition; generate a clinical trial patient population from the candidate patients, and exclude the respective candidate patient from the clinical trial population based on evaluating the statistical variation against a threshold variation defined by a patient model.

In one embodiment, the analysis component is further configured to determine a confidence level associated with expected trial results. In one embodiment, the confidence level includes an evaluation of whether the candidate patient will complete the clinical trial regimen. In one embodiment, the confidence level includes an evaluation of whether the clinical trial results will be significant.

Still other aspects, embodiments and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment. References to "an embodiment," "an example," "some embodiments," "some examples," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearances of such terms herein are not necessarily all referring to the same embodiment.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

At least some embodiments disclosed herein include apparatus and processes for selecting, monitoring, and screening potential patient populations for clinical trials. According to some embodiments, the systems and methods are configured to execute pre-treatment monitoring to capture detailed patient histories. The systems and methods analyze the detailed patient histories against selection criteria for a given trial or specified for a specific population. In some embodiments, the selection criteria can be specified as a selection profile (e.g., for a specific trial, specific population, defined based on trial criteria, defined on generic health characteristics, etc.). The detailed history can also be analyzed to identify variation within initially qualifying populations. Qualifying patients with widely varying responses, for example, to ongoing treatments, may generate trial results that are masked by the patient's varying responses. The system can identify and filter such patients from the candidate pool ensuring better representative results.

According to other embodiments, pre-enrollment processing of potential patient populations enables faster identification and significant reduction in actual enrollment into a clinical trial. For example, systematic efficiency is achieved by identifying ideal patient populations (including randomly selected populations). In some examples, the patient population size can be significantly reduced based on pre-qualification criteria. In one embodiment, the pre-qualification system reduces the volume of patient candidates that need to participate in a clinical trial based on a determined confidence associated with the pre-trial assessment and modeling of suitable patient characteristics. The overall effect enables the system to reduce the computations, collection, and/or communication of data that would be required under conventional approaches.

According to one embodiment, once potential patients confirm their interest in a pre-treatment phase, the qualifying patients can be contacted through the system at once, allowing an actual trial phase to begin as soon as enough qualifying patients respond. Thus, various embodiments of the system increase execution efficiency over conventional approaches. Additionally, patients interested in participating in the clinical trial can be pre-consented, for example, during execution of the pre-treatment phase. In conventional settings, consent to participate is a high pressure and difficult event, where patients are expected to read, understand, and sign lengthy legal documents as part of enrolling in a clinical trial. Providing potential patients the opportunity to review and execute the lengthy consent agreement during pre-treatment phases allows patients to review such document in the comfort of their own home and/or with the advice of family, friends, and physicians.

According to some aspects and embodiments, the system is configured to speed patient enrollment. There is long felt unmet need in the industry to decrease clinical trial enrollment times. Slow patient enrollment and the resulting delays are one of the biggest problems in clinical research. For example the lost sales and wasted opportunities for a blockbuster drug due to slow trials have been estimated at over $2.6 billion. Many trials fail to enroll their target number of patients, and have to make do with a smaller number of patients. The effect is an under-powered study that fails to meet clinical trial endpoints. Further, the smaller patient pool results in wider confidence intervals that can lead directly to erroneous conclusions.

Patients' enrollment can represent problems for regulators and institutional review boards (IRBs"). If a treatment happens to be harmful to patients, slow enrollment and delayed trial execution means that ascertaining that harm is delayed for a period of time during which patients are unnecessarily exposed to a damaging drug.

In some embodiments, system based pre-enrollment is configured to facilitate the inclusion of minorities and sub-populations in the clinical trials. The system enables selection of patients so that the patient pool better resembles the general population. The system further provides for better ethnic diversity among patients pool, and can also be configured to ensure better representation of vulnerable populations. In further embodiments, the system can identify patients with uncommon gene variations and enable patient pre-qualification/selection. For example, in the case of targeted medicines, pre-enrollment will facilitate the inclusion of the patients with uncommon gene variations.

In further embodiments, clinical trial patients are better matched to respective treatments based on system modeling and/or filtering. For example, trial sponsors will know ahead of enrollment which patients are stable; which ones are severely (or lightly) affected; which ones are degrading fast or slowly. Thus, the system enables improved selection of the patients that can benefit from the treatments. In yet other embodiment, the system facilitates research in rare diseases—which affect 30 million Americans. The system resolves issues around poor availability of patients that makes clinical research even more challenging.

Examples of the methods and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, components, elements and features discussed in connection with any one or more examples are not intended to be excluded from a similar role in any other examples.

Also, the phraseology and terminology used herein is for the purpose of description and should not be regarded as limiting. Any references to examples, embodiments, components, elements or acts of the systems and methods herein referred to in the singular may also embrace embodiments including a plurality, and any references in plural to any embodiment, component, element or act herein may also embrace embodiments including only a singularity. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Figure 1:
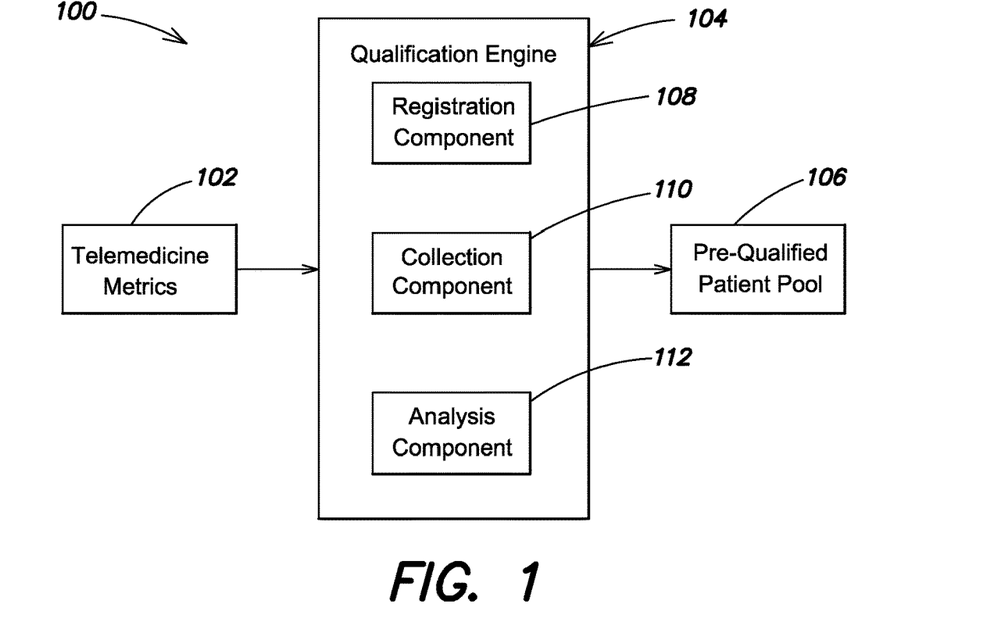
FIG. 1 is a block diagram of an example qualification system, including a qualification engine, according to one embodiment.

Referring to FIG. 1, there is illustrated one example of a qualification system 100 for screening potential clinical trial candidates using a qualification engine 104. Health metrics 102 obtained from telemedicine devices can be communicated to the qualification system 100 and/or qualification engine 104. The system and/or engine can analyze the received health metrics (e.g., 102) to identify a prequalified patient pool 106. Elements of the system 100 can be provided using a computing system such as the computer systems 400 and/or 402 described with reference to FIG. 4.

In some embodiments, the system 100 is configured to execute a pre-treatment "clinical trial" measuring health characteristics of candidate participants. The monitoring devices used and the health characteristics measured can be selected based on the health characteristics that will be measured during actual execution of the clinical trial. The system can be configured to monitor the same physiological characteristics/behaviors that are defined for evaluating the actual execution of the clinical trial. In other embodiments, specific characteristics of disease progression and/or diagnosis can be used to further filter candidate patient populations.

According to one embodiment, a qualification system 100 and/or engine 104 can include a registration component 108 configured to accept user registrations. In order to participate in pre-treatment qualification, candidate patients can be required to register with the system 100. In some embodiments, the system 100 can be accessible over a communication network (e.g., the Internet). In one example, the candidate patients can access the system 100 via a computer system executing a browser program. The candidate patients can register with the system 100 once connected. In some embodiments, registration can require invitation, either through a physician or directly to a patient having a disease or ailment that will be the subject of a clinical trial.

In some embodiments, the candidate patients can connect to the system 100 and the registration component 108 can be configured to confirm existing patient information, capture additional information, and obtain consent to participate in pre-treatment phases. In some examples, patients' consent to participate includes consent for access to any existing medical records and/or information. According to one embodiment, the registration component 108 can also be configured to pair candidate patients with one or more telemedicine devices. The specific device can be pre-selected, or identified by the registration component based on system parameters for a given pre-treatment trial. For example, heart rate monitors, blood pressure monitors, activity monitors can be paired with candidate patients and delivered. In some implementations, telemedicine devices can be delivered directly to candidate patients. In others, the monitoring devices are delivered to a treating physician for distribution to the candidate patients.

In some settings, the telemedicine devices include applications that can be executed on mobile devices (e.g., smart phones, tablets, netbooks, e-readers, etc.). Registration and delivery can be as simple as downloading an "app" for execution on a smart phone. In some embodiments, the app can be configured to measure various physiological markers (e.g., based on user interaction, an app can measure vision, visual acuity, touch sensitivity, hearing, speech, mobility, activity level, human output (e.g., waste) tracking, etc.) In various other embodiments, the app can capture data from monitoring devices (e.g., blood pressure monitor, EKG monitors (e.g., heart or head), heart rate monitor, weight monitor, temperature monitors, fluid monitors, etc.).

According to one embodiment, the registration component 108 can also manage registration of pre-treatment trial administrators. Further, the registration component 108 can be configured to enable the administrators to define specific characteristics of patient populations to include and/or invite as candidates, medical characteristics to evaluate to qualify, and any further filter criteria (including, for example, treatment outcome information (e.g., progressing disease under current treatment, stable under current treatment, etc.). The administrators can identify the telemedicine monitoring devices to use for pre-treatment execution (e.g., pill counters, activity monitors, heart, blood pressure sensors, oxygen sensors, software applications, etc.). The telemedicine devices can be configured to report collected information (e.g., 102) automatically to the system 100.

In some embodiments, system 100 and/or engine 104 can include a collection component 110 configured to receive information from telemedicine devices. In some embodiments, the collection component 110 can be configured to poll the devices to capture medical information. In other embodiments, automated information collection systems (e.g., telemedicine devices and/or collection component 110) can automatically communicate medical information, thus simplifying data acquisition from both the system and patient perspective. The captured data can then be analyzed by the system to ensure careful and accurate selection of patients for a trial pool of patients. In some implementations, the system generates detailed and comparable information about patient characteristics (e.g., disease progression, physiological characteristics, physiological symptoms, etc.) for each potential candidate.

According to one embodiment, potential candidates are enrolled in a pre-trial certification period. The period can be defined on the system by the administrators. The potential candidates can be selected based on an indication of willingness to participate in clinical research. Various candidate pools can be defined based on the type of research for which the patient is willing to participate. The system invites such patients for specific pre-treatment testing.

As discussed, telemedicine monitoring devices can be selected and distributed to potential candidates for monitoring target medical information. In one example, MS disease progression can be reviewed for evaluating a potential candidate population for desired criteria. The telemedicine devices (e.g., blood pressure monitors, drug distribution monitors, EEG sensors, etc.) can capture detailed objective clinical history for each candidate.

In one example, smart phones, portable computing devices, or wireless recorders (e.g., Fibit) can be used to track patients' mobility, their ability to sustain effort, climb stairs, move without pausing, including the frequency and duration of their pauses, etc. This clinical history, in turn, enables the system to match such potential candidates precisely to the characteristics that would help scientists developing drugs for diseases that impair mobility (claudication, MS, CFS, etc). In some embodiments, the system enables scientists and/or clinicians to match candidate trial participants to a patient characteristic profile. The patient characteristic profile can be defined to include a specification of a disease and can also include further specification of disease progression.

According to various embodiments, a patient model can be generated based on tracking and/or evaluating patient visual acuity. In one example, the pre-qualification system tracks visual acuity information as an indicator of Multiple Sclerosis ("MS"). In one embodiment, characteristics of the tracked patient population can be used to identify patient symptoms that fall outside of expected ranges and/or qualify as outlier symptoms or responses (e.g., in terms of severity, frequency, duration, consistency, etc.). In one example, the outlier patients can be filtered from a clinical trial. In another example, the clinical trial can be keyed to patients who have inconsistent and/or outlier responses, thus, the patient model and inclusion criteria can be used to specifically target fluctuation symptomology as a modeled characteristic.

In another example, an app can be distributed to candidate patients and configured to analyze vocal patterns for voice tremors. In one embodiment, a patient model can be generated based on analyzing voice and speech to identify any voice tremor as associated with Parkinson's disease. In a further example, the pre-qualification system can identify patients with consistent Parkinson's symptoms either with treatment or without. In some embodiments, consistent symptoms can include progressive worsening, improvement in symptoms, stability of symptoms, etc. In one example, the system analyzes patient symptoms to determine that a rate of change is consistent with other data captured for the candidate population. In another example, the system analyzes patient symptoms to identify outlier measurements, and to identify outlier symptom measurements where the average progression of symptoms falls within expected ranges.

Various other patient models can be used to identify and track patient medical information and/or symptoms. Various devices and various combinations of devices can be registered on the system to enable accurate and precise measurement. In some embodiments, blood pressure monitors can be issued to participating candidates. The blood pressure tracking can be used by the system to model hypertension symptoms. Based on symptom readings, various candidate patients can be included and/or excluded from trial participation. In further embodiments, patient models can be linked to specific treatments and response characteristics. In one example, poor responses to conventional treatments can be used to identify candidates for new approaches.

According to another example, a device for capturing data on pulmonary function can be distribution and response information collected. Pulmonary Function test ("PFTs") can be executed by the system and/or apps distributed from the system to measure systems of Chronic obstructive pulmonary disease ("COPD"). In further embodiments, the system can capture information on walking ability of a group of candidate patients (e.g., using GPS elements in a smart phone or other distributed monitoring device). The system can monitor symptoms of Duchenne muscular dystrophy ("DMD") based on measuring walking ability.

In further embodiments, the system can be configured to distribute and/or register sleep monitoring devices (e.g., wearable headbands to monitor brain activity, constriction sensors to monitor breathing, video capture devices to monitor activity during sleep, etc.). The system can be configured to collect and analyze quality of sleep and associated measurements of sleep data with depression symptoms.

According to various embodiments, and combination of sensors and any data capture device (including for example, various combinations, subsets, etc. of the sensors and applications described above) can be registered on the system and pre-qualification data can be automatically captured. In some settings healthy patients, patients without symptoms, etc., can be included in the pre-qualification populations. In some settings potential placebo effect can be measured on the healthy patients to provide reference and/or additional reference points for identifying outlier placebo effect patients within a segment having a condition being considered for clinical trial.

The detailed clinical history generated by the system enables testing of precisely defined patient populations. In one example, scientist may want to test the drug in severely affected, but stable patients. In another example, a scientist can select patients with decreasing response to a specific treatment (e.g., increasing symptomology). Various embodiments of the system capture detailed clinical history that enable matching of such precise patient profile information. In another example, the system can match against a profile where a given disease is progressing the fastest. According to one aspect, the data gathered by the system in a pre-treatment phase enables the selection by the system of these qualifying patients. Further, it is realized that such precision in patient selection is not achievable in conventional approaches, including conventional run-in implementation. According to some aspects, the level of precision the pre-qualification system executes reduces the overall needed size of any clinical trial patient population. In one example, more precise patient selection enables the system to utilize or capture a smaller volume of data while achieving the same or better confidence level in the clinical trial results as a conventional trial using many times the patient population.

According to one embodiment, the system and/or engine 104 can include an analysis component 112 configured to compare monitored health information to patient models defined for respective clinical trials. The patient models can be defined by trial administrators (e.g., using registration component 108). The administrator can define, for example, any one or more of a specific ailment, disease, symptom, current therapy, current drug, course of treatment, or other criteria which will be targeted by a clinical trial. The patient profile can be used by the system to filter candidate patients having the pre-requisites. With patients having the particular disease, ailment, symptom, current therapy, current drug, course of treatment, or other criteria, the administrator can also define targets for measuring health information. For example, for a blood pressure treatment trial, the administrators can require that qualified candidate patient have consistently high blood pressure over a period of time. In other examples, a clinical trial may be targeting high blood pressure coupled with other symptoms. Thus, the administrators can tailor pre-requisites in the patient profile and/or monitored data targets in the profile to meet any requirements of a given trial.

Additionally, the analysis component 112 can be configured to further analyze monitored health information within the candidate patients who qualify under defined pre-requisites and meet monitored target. The further analysis can identify statistical outliers within the qualifying population. For example, filtering out patients with highly variable readings can increase the likelihood that changes in measurements during a clinical trial execution are significant, and not the result of variability in the subject patient. Further, the analysis component 112 can also be configured to identify statistical outliers based on monitored health information. In some examples, the analysis component can be configured to identify and exclude such outlier candidates. According to one embodiment, excluding statistical outliers provides a more homogenous population of qualified candidate patients.

Figure 2:
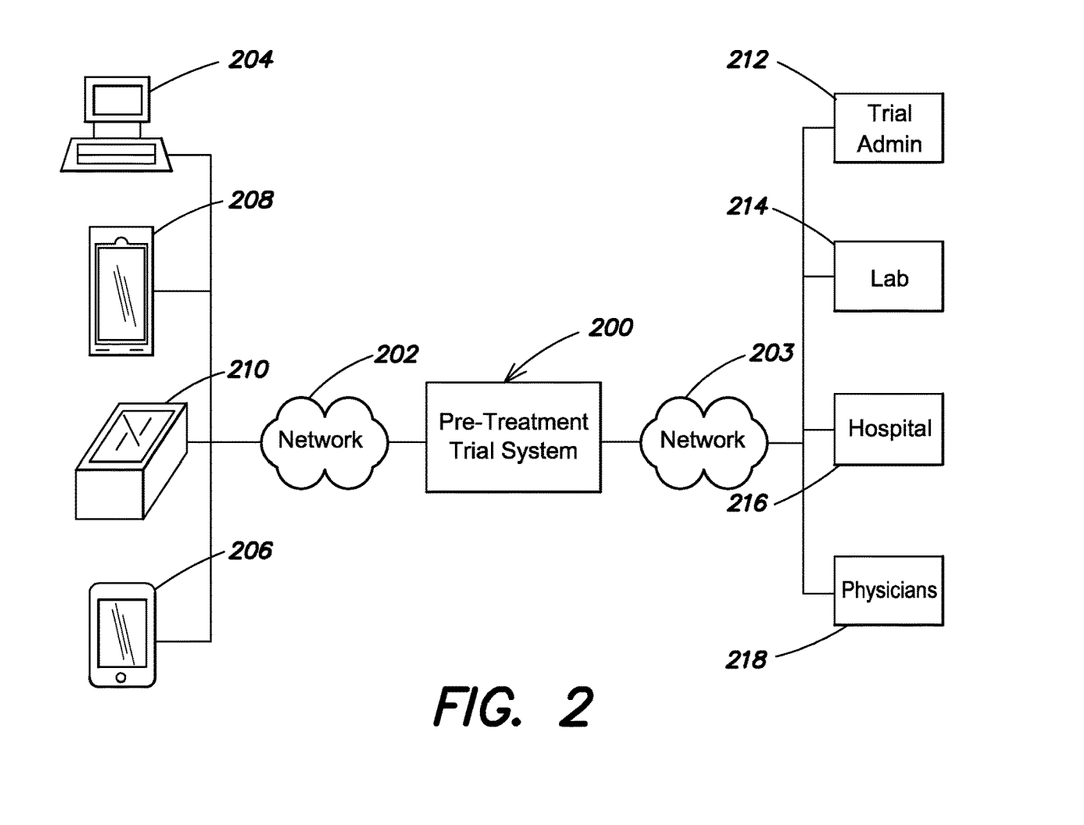
FIG. 2 is a block diagram of an example qualification system, according to one embodiment.

Shown in FIG. 2 is a block diagram of an example pre-treatment monitoring system 200. The pre-treatment monitoring system 200 can include a qualification subsystem and/or engine (e.g., 100 and 104) and/or the components discussed above. The pre-treatment execution system 200 provides a web based interface for candidate patients through a communication network 202. The candidate patients can interact with the monitoring system 200 via respective host computer systems 204, mobile devices (e.g., smart phones 206, tablets 208). The candidate patients can register with the system 200, and receive monitoring devices (e.g., 210—blood pressure sensor) for capturing and reporting health information. As discussed, some monitoring devices provided can include applications for download that utilize native sensors in the candidate patients' smart phones or tablets to capture and communicate health information (e.g., activity monitoring applications).

Pre-treatments trial administrators (e.g. 212) can also interface with the system 200 through a communication network (e.g., 203). The administrators can access the system 200 through any combination of private networks and/or public networks (e.g. the Internet). In some examples, the administrators can use browser programs to interact with the system 200. Once connected, the administrators can define patient population criteria for a respective clinical trial. In some embodiments, the system can be configured to track multiple trials and respective testing criteria. The administrators can include laboratories (e.g., 214), hospitals (e.g., 216), and/or physicians (e.g., 218).

For each pre-treatment trial, the administrators can define what health characteristics will be monitored and/or what devices will be used during pre-treatment execution or qualification phases for the respective trials. Further, patient profiles can be defined on the system and target measurements defined to qualify candidate patients. The system 200 can then compare monitored health information, automatically reported by the telemedicine devices, against any defined criteria. In some embodiments, the administrators can define a length of time associated with a pre-treatment qualification phase. Once the period expires, the system 200 can identify qualified patients for review by the administrators. In further embodiments, trial administrators can further refine a qualified patient pool using system 200. The administrators may alter defined parameters on statistical outliers (e.g., exclude patients occurring on the outer 5% of a distribution of monitored health information) to increase or decrease a qualified patient pool.

Figure 3:
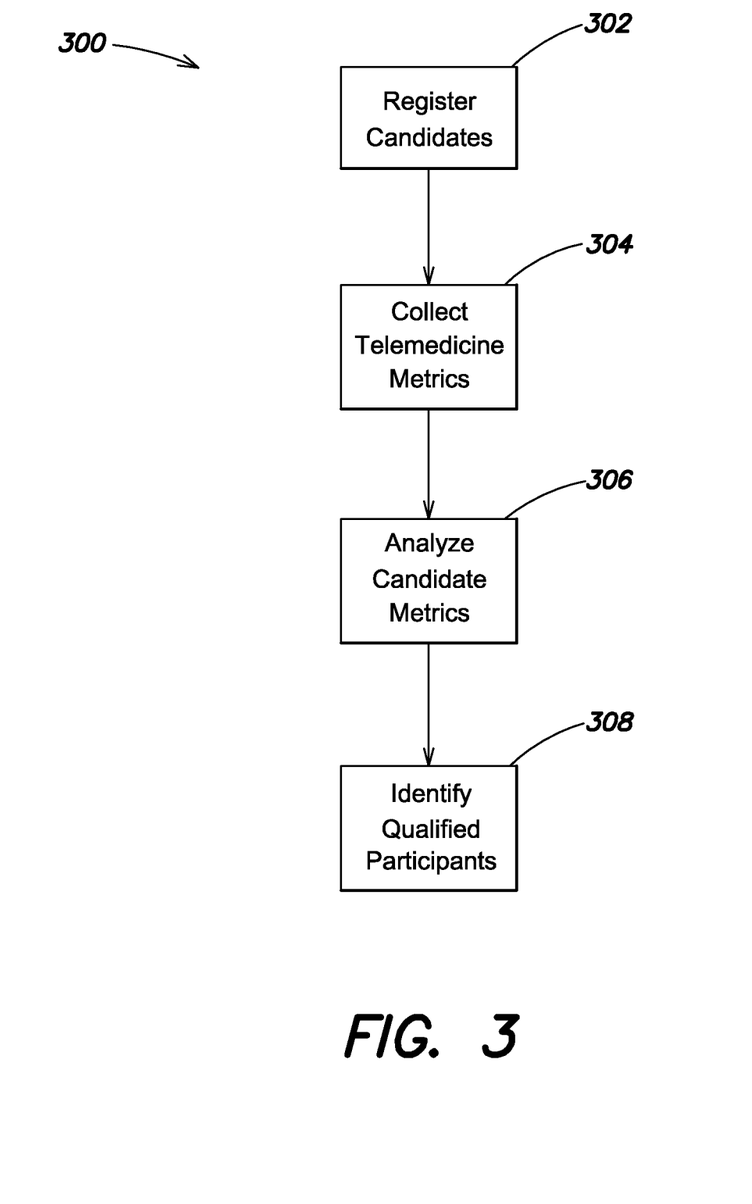
FIG. 3 is an example process flow for a method of pre-enrolling patients for clinical trials, according to one embodiment.

Once a qualified patient pool is identified, the administrators can invite the qualified patients to participate in an actual clinical trial execution including treatment options. As discussed, a qualification and/or monitoring system (e.g., 100 and 200) can be configured to execute a variety of processes to pre-qualify clinical trial patient populations. FIG. 3 illustrates an example process flow 300 for pre-qualifying clinical trial patient populations.

The process 300 begins at 302 with candidate registration. In some examples, candidates can be identified by their treating physicians and recommend to trial administrators as potential candidate patients. In other examples, candidates can be solicited through treating physician or can identify themselves via other conventional means. Registration at 302 can include capturing existing patient history information to determine that the candidate meets pre-registration criteria (e.g., has the disease, ailment, symptom, etc., to be analyzed during a clinical trial). According to some embodiments, registration at 302 can also include associating candidates with monitoring devices for executing the pre-treatment qualification phase. For example, smart phone apps can be made available for download and monitoring devices can be delivered to patients and/or treating physicians as part of 302.

Once the monitoring devices are delivered or respective software downloaded, process 300 can continue at 304 with collection of telemedicine metrics. Depending on the devices delivered and/or downloaded a variety of health information data can be reported automatically on the candidate patients. Process 300 continues at 306 with analysis of the collected health information. The health information can be compared at 306 to any criteria specified by the administrators of the pre-treatment phase. In some embodiments, analysis at 306 can include comparison to a patient model, disease progression characteristics, treatment response characteristics, etc. Based on the analysis, qualified participants are identified at 308. The qualified participant pool can be invited to participate in an actual clinical trial execution.

As discussed above with regard to FIG. 1, various aspects and functions described herein may be implemented as specialized hardware or software components executing in one or more computer systems. There are many examples of computer systems that are currently in use. These examples include, among others, network appliances, personal computers, workstations, mainframes, networked clients, servers, media servers, application servers, database servers and web servers. Other examples of computer systems may include mobile computing devices, such as cellular phones and personal digital assistants, and network equipment, such as load balancers, routers and switches. Further, aspects may be located on a single computer system or may be distributed among a plurality of computer systems connected to one or more communication networks.

For example, various aspects and functions may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Consequently, examples are not limited to executing on any particular system or group of systems. Further, aspects and functions may be implemented in software, hardware or firmware, or any combination thereof. Thus, aspects and functions may be implemented within methods, acts, systems, system elements and components using a variety of hardware and software configurations, and examples are not limited to any particular distributed architecture, network, or communication protocol.

Figure 4:
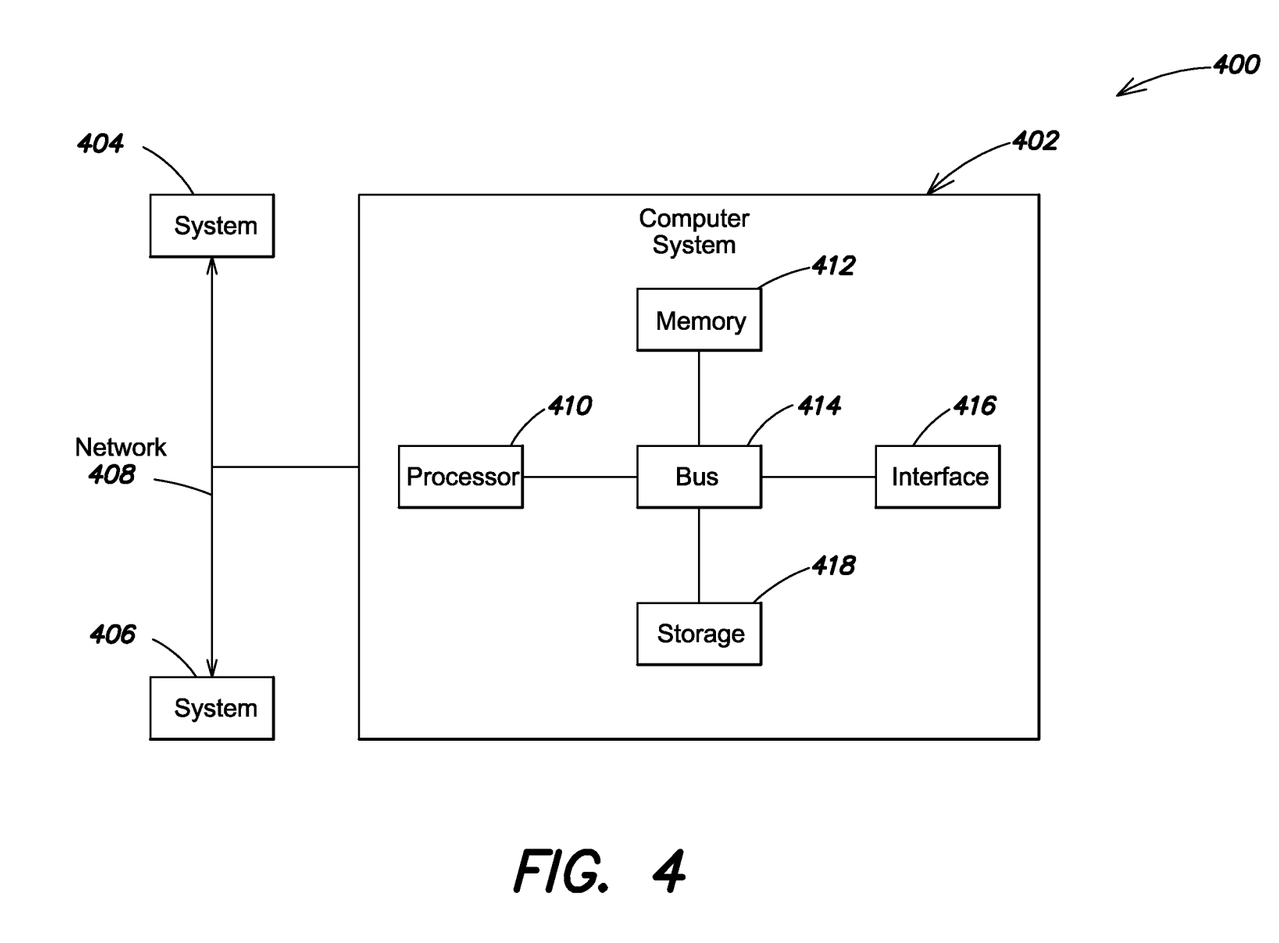
FIG. 4 is a block diagram of a general purpose computer system which may be specially configured as disclosed to implement various aspects of the disclosure.

Referring to FIG. 4, there is illustrated a block diagram of a distributed computer system 400, in which various aspects and functions are practiced. As shown, the distributed computer system 400 includes one more computer systems that exchange information. More specifically, the distributed computer system 400 includes computer systems 402, 404 and 406. As shown, the computer systems 402, 404 and 406 are interconnected by, and may exchange data through, a communication network 408. For example, a qualification system and/or engine can be implemented on 402, to provide functions as discussed herein.

In some embodiments, the network 408 may include any communication network through which computer systems may exchange data. To exchange data using the network 408, the computer systems 402, 404 and 406 and the network 408 may use various methods, protocols and standards, including, among others, Fibre Channel, Token Ring, Ethernet, Wireless Ethernet, BLUETOOTH wireless, IP, IPV6, TCP/IP, UDP, DTN, HTTP, FTP, SNMP, SMS, MMS, SS7, JSON, SOAP, CORBA, REST and Web Services. To ensure data transfer is secure, the computer systems 402, 404 and 406 may transmit data via the network 408 using a variety of security measures including, for example, TLS, SSL or VPN. While the distributed computer system 400 illustrates three networked computer systems, the distributed computer system 400 is not so limited and may include any number of computer systems and computing devices, networked using any medium and communication protocol.

As illustrated in FIG. 4, the computer system 402 includes a processor 410, a memory 412, a bus 414, an interface 416 and data storage 418. To implement at least some of the aspects, functions and processes disclosed herein, the processor 410 performs a series of instructions that result in manipulated data. The processor 410 may be any type of processor, multiprocessor or controller. Some exemplary processors include commercially available processors such as an Intel XEON processor, ITANIUM processor, CORE processor, CELERON processor, or PENTIUM processor, an AMD OPTERON processor, a Sun ULTRASPARC processor or IBM Power5+ processor and an IBM mainframe chip. The processor 410 is connected to other system components, including one or more memory devices 412, by the bus 414.

The memory 412 stores programs and data during operation of the computer system 402. Thus, the memory 412 may be a relatively high performance, volatile, random access memory such as a dynamic random access memory (DRAM) or static memory (SRAM). However, the memory 412 may include any device for storing data, such as a disk drive or other non-volatile storage device. Various examples may organize the memory 412 into particularized and, in some cases, unique structures to perform the functions disclosed herein. These data structures may be sized and organized to store values for particular data and types of data.

Components of the computer system 402 are coupled by an interconnection element such as the bus 414. The bus 414 may include one or more physical busses, for example, busses between components that are integrated within a same machine, but may include any communication coupling between system elements including specialized or standard computing bus technologies such as IDE, SCSI, PCI and InfiniBand. The bus 414 enables communications, such as data and instructions, to be exchanged between system components of the computer system 402.

The computer system 402 also includes one or more interface devices 416 such as input devices, output devices and combination input/output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system 402 to exchange information and to communicate with external entities, such as users and other systems.

The data storage 418 includes a computer readable and writeable nonvolatile, or non-transitory, data storage medium in which instructions are stored that define a program or other object that is executed by the processor 410. The data storage 418 also may include information that is recorded, on or in, the medium, and that is processed by the processor 410 during execution of the program. More specifically, the information may be stored in one or more data structures specifically configured to conserve storage space or increase data exchange performance.

The instructions stored in the data storage may be persistently stored as encoded signals, and the instructions may cause the processor 410 to perform any of the functions described herein. The medium may be, for example, optical disk, magnetic disk or flash memory, among other options. In operation, the processor 410 or some other controller causes data to be read from the nonvolatile recording medium into another memory, such as the memory 412, that allows for faster access to the information by the processor 410 than does the storage medium included in the data storage 418. The memory may be located in the data storage 418 or in the memory 412, however, the processor 410 manipulates the data within the memory, and then copies the data to the storage medium associated with the data storage 418 after processing is completed. A variety of components may manage data movement between the storage medium and other memory elements and examples are not limited to particular data management components. Further, examples are not limited to a particular memory system or data storage system.

Although the computer system 402 is shown by way of example as one type of computer system upon which various aspects and functions may be practiced, aspects and functions are not limited to being implemented on the computer system 402 as shown in FIG. 4. Various aspects and functions may be practiced on one or more computers having different architectures or components than that shown in FIG. 4. For instance, the computer system 402 may include specially programmed, special-purpose hardware, such as an application-specific integrated circuit (ASIC) tailored to perform a particular operation disclosed herein. While another example may perform the same function using a grid of several general-purpose computing devices running MAC OS System X with Motorola PowerPC processors and several specialized computing devices running proprietary hardware and operating systems.

The computer system 402 may be a computer system including an operating system that manages at least a portion of the hardware elements included in the computer system 402. In some examples, a processor or controller, such as the processor 410, executes an operating system. Examples of a particular operating system that may be executed include a Windows-based operating system, such as, WINDOWS NT operating system, WINDOWS 2000 operating system (WINDOWS ME operating system), WINDOWS XP operating system, WINDOWS Vista operating system or WINDOWS 7 or 8 operating systems, available from the Microsoft Corporation, a MAC OS System X operating system available from Apple Computer, one of many Linux-based operating system distributions, for example, the Enterprise Linux operating system available from Red Hat Inc., a Solaris operating system available from Sun Microsystems, or a UNIX operating systems available from various sources. Many other operating systems may be used, and examples are not limited to any particular operating system.

The processor 410 and operating system together define a computer platform for which application programs in high-level programming languages are written. These component applications may be executable, intermediate, bytecode or interpreted code which communicates over a communication network, for example, the Internet, using a communication protocol, for example, TCP/IP. Similarly, aspects may be implemented using an object-oriented programming language, such as .NET language, SMALLTALK language, JAVA language, C++ language, ADA language, C# (C-Sharp) language, OBJECTIVE C language, or JAVASCRIPT language. Other object-oriented programming languages may also be used. Alternatively, functional, scripting, or logical programming languages may be used.

Additionally, various aspects and functions may be implemented in a non-programmed environment, for example, documents created in HTML, XML or other format that, when viewed in a window of a browser program, can render aspects of a graphical-user interface or perform other functions. For example, an administration component can render an interface in a browser to enable definition of contamination risks.

Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Accordingly, the functional components disclosed herein may include a wide variety of elements, e.g., specialized hardware, executable code, data structures or objects, that are configured to perform the functions described herein.

In some examples, the components disclosed herein may read parameters that affect the functions performed by the components. These parameters may be physically stored in any form of suitable memory including volatile memory (such as RAM) or nonvolatile memory (such as a magnetic hard drive). In addition, the parameters may be logically stored in a propriety data structure (such as a database or file defined by a user mode application) or in a commonly shared data structure (such as an application registry that is defined by an operating system). In addition, some examples provide for both system and user interfaces that allow external entities to modify the parameters and thereby configure the behavior of the components.

Having thus described several aspects of at least one example, it is to be appreciated that various alterations, modifications, and improvements will readily occur to those skilled in the art. For instance, examples disclosed herein may also be used in other contexts. Such alterations, modifications, and improvements are intended to be part of this disclosure, and are intended to be within the scope of the examples discussed herein. Accordingly, the foregoing description and drawings are by way of example only.

What is claimed is:

1. A system for prequalifying clinical trial patient populations, the system comprising:
   at least one processor operatively connected to a memory and configured to:
   register candidate patients and associate remote monitoring devices to registered patients for a defined clinical trial, wherein at least one of the remote monitoring devices is wearable and configured to monitor at least one of vision, visual acuity, touch sensitivity, hearing, speech, mobility, activity level, waste output, mobility, exertion, blood pressure, heart rate, or brain activity;
   connect with the remote monitoring devices via at least one encrypted network interface and automatically receive health information from the remote monitoring devices over a period of time, the health information comprising physiologic or biometric data on the registered candidate patients including measurements indicating at least one of vision, visual acuity, touch sensitivity, hearing, speech, mobility, activity level, waste output, mobility, exertion, blood pressure, heart rate, or brain activity of the registered candidate patients;
   qualify, based on one or more uncommon gene variations, one or more patients from among the registered candidate patients at least by identifying the one or more uncommon gene variations in the one or more patients; and
   qualify, based on the health information received over the period of time, patients from among the registered candidate patients according to a patient model at least by:
   identifying statistical variation in a deviation on measurements monitored by the remote monitoring devices over time for an individual respective registered patient, wherein the measurements and the statistical variation are specific to the individual respective registered patient,
   generating a clinical trial patient population from the registered patients, and
   excluding the individual respective registered patient from the clinical trial patient population based on evaluating the statistical variation against a threshold statistical variation over time defined by the patient model,
   wherein the patient model further defines a first characteristic for a disease or ailment, and further defines at least a second characteristic associated with disease progression or response to current treatment; and
   determine a confidence level associated with expected trial results, the confidence level including a first evaluation of whether a respective registered patient will complete the clinical trial regimen and a second evaluation of whether the clinical trial results will be significant.

2. The system according to claim 1, wherein the at least one processor is further configured to manage patient consent to participate in a clinical trial.

3. The system according to claim 2, wherein the system is further configured to communicate to a qualified candidate patient pool to start the clinical trial.

4. The system according to claim 1, wherein the system is configured to accept definition of a patient model based on medical characteristics to evaluate during execution of the clinical trial.

5. The system according to claim 1, wherein the at least one processor is further configured to identify improper candidates responsive to variations in the received health information.

6. The system according to claim 1, wherein the at least one processor is further configured to generate the threshold statistical variation responsive to analyzing the stored health information.

7. The system according to claim 6, wherein the at least one processor is further configured to:
   analyze historical patient data having common characteristics defined by a patient model;
   test the historical patient data against all historical patient data; and
   generate the threshold statistical variation to exclude any candidate patient having one or more measurements exceeding two standard deviations from historical patient data.

8. The system according to claim 1, wherein the at least one processor is further configured to generate the patient model responsive to analyzing stored health information and any associated condition.

9. The system according to claim 1, wherein the at least one processor is further configured to manage patient consent to participate in a clinical trial.

10. The system according to claim 1, wherein the symptoms or physiologic condition comprise at least one of a state, a change, or a rate of change in at least one of:
    mobility, exertion,
blood pressure,
respiration,
heart rate,
brain activity, and
tactile response or sensation.

11. The system according to claim 1, wherein the at least one processor is further configured to:
  identify and exclude, from among the registered candidate patients, patients that respond under a placebo effect.

* * * * *